United States Patent [19]
McCullough

[11] Patent Number: 5,486,289
[45] Date of Patent: Jan. 23, 1996

[54] SYSTEM FOR MECHANICALLY STABILIZING A BED OF PARTICULATE MEDIA

[75] Inventor: Edward D. McCullough, Riverside, Calif.

[73] Assignee: Rockwell International Corporation, Seal Beach, Calif.

[21] Appl. No.: 301,106

[22] Filed: Sep. 6, 1994

[51] Int. Cl.⁶ .......................... B01D 15/04; B01D 15/08; B01D 53/02

[52] U.S. Cl. .......................... 210/289; 210/350; 210/351; 210/198.2

[58] Field of Search .......................... 210/289, 291, 210/198.2, 198.3, 350, 351, 352

[56] References Cited

U.S. PATENT DOCUMENTS

| | | | |
|---|---|---|---|
| 3,180,825 | 4/1965 | Couvreur et al. | 210/30 |
| 3,487,938 | 1/1970 | Patterson | 210/198 |
| 4,238,325 | 12/1980 | Heskett | 210/678 |
| 4,294,699 | 10/1981 | Herrmann | 210/287 |
| 4,350,595 | 9/1982 | Gunkel | 210/656 |
| 4,400,278 | 8/1983 | Martinola | 210/678 |
| 4,597,866 | 7/1986 | Couillard | 210/198.2 |
| 4,776,962 | 10/1988 | Wakeman | 210/748 |
| 4,971,688 | 11/1990 | Francois et al. | 210/350 |
| 5,169,522 | 12/1992 | Shalon et al. | 210/198 |
| 5,378,361 | 1/1995 | Baeckström | 210/198.2 |

Primary Examiner—Cynthia L. Nessler
Attorney, Agent, or Firm—Lawrence N. Ginsberg; Charles T. Silberberg

[57] ABSTRACT

A system for mechanically stabilizing a bed of particulate media which undergoes changes in volume during operation. A tubular column is provided which is closed and ported at a first end and open at a second end. A piston assembly is supported in the column for containing a bed of particulate media. The piston assembly comprises a piston having at least one opening for conveying a fluid through the piston. A fluid connection is attached to the piston in fluid communication with the opening. The fluid connection may move relative to the tubular column. A resilient seal is arranged about the piston to provide sealing engagement of the piston and the tubular column and to provide proper alignment therebetween. Porous barrier elements are positioned in the column so as to prevent the undesired escape of particulate media through the tubular column port and through the piston opening. The tubular column port and fluid connection are connectable to either a source of fluid or vacuum so that fluid can be drawn through the bed in either direction generally parallel to the longitudinal axis of the tubular column, at a pressure below ambient, thereby causing the piston to respond to changes in volume of the particulate media so as to continually compress and compact the particulate media regardless of the direction of fluid flow.

4 Claims, 2 Drawing Sheets

SYSTEM FOR MECHANICALLY STABILIZING A BED OF PARTICULATE MEDIA

BACKGROUND OF THE INVENTION

1. Field of the Invention

This invention relates to the mechanical stabilization of particulate media, and more particularly to the use of a piston in maintaining a bed in a compacted state throughout its operation to enhance bed performance.

2. Description of the Related Art

Column performance of ion exchange and other particulate media during column elution can be improved if the material is taken off the column in a direction which is the reverse of that which was used for loading. This results in a more concentrated eluant. This process is impeded by the propensity of the bed material to channel under reverse flow when compacted by gravitation force only. What is needed is a method of compressing the bed to prevent channeling while allowing for expansion and contraction of the bed.

U.S. Pat. No. 5,169,522, issued to Y. Shalon et al. discloses a method for compressing beds of particles for use in chromatographic columns which consist of a metallic piston in a metallic cylinder which provides for pressurization of the piston in order to compress the bed. The method requires the cylinder to be flanged on both ends with the piston inside. It requires penetration of the flange to convey the fluid through the flexible tubing to the piston and also penetration of the flange to airload or pressurize the piston with the gas.

U.S. Pat. No. 4,597,866, issued to F. Couillard, discloses a chromatographic column assembly comprising a tubular column with both ends sealed. An internal piston is used to compress a particulate bed. The compressive force results from gas loading of the piston. It requires a pressurizing system and the column to be sealed at both ends.

SUMMARY OF THE INVENTION

The present invention is a system for mechanically stabilizing a bed off particulate media which undergoes changes in volume during operation. A tubular column is provided which is closed and ported at a first end and open at a second end. A piston assembly is supported in the column for containing a bed of particulate media. The piston assembly comprises a piston having at least one opening for conveying a fluid through the piston. A fluid connection is attached to the piston in fluid communication with the opening. The fluid connection may move relative to the tubular column. A resilient seal is arranged about the piston to provide sealing engagement of the piston and the tubular column and to provide proper alignment therebetween. Porous barrier elements are positioned in the column so as to prevent the undesired escape of particulate media through the tubular column port and through the piston opening. The tubular column port and fluid connection are connectable to either a source of fluid or vacuum so that fluid can be drawn through the bed in either direction generally parallel to the longitudinal axis of the tubular column, at a pressure below ambient, thereby causing the piston to respond to changes in volume of the particulate media so as to continually compress and compact the particulate media regardless of the direction of fluid flow. In a preferred embodiment, the particulate media comprises ion exchange resin. In another embodiment the particulate media comprises a bed of desiccant. The fluid connection preferably comprises flexible tubing.

The present invention has fewer parts than the prior art devices. It does not require a flange with multiple penetrations to seal off a pressurized section. No pressurization system is required. Instead, the differential pressure between ambient and the pressure in the bed media provides the force for compressing the particulate media. Therefore, the column need be sealed at one end only. The operation of this system is simpler as no air loading of the piston is required. Additionally, since there is no pressurized section, there is no possibility of explosion of organic vapors. Vacuums or siphons are used to move fluids through the system.

The present system operates below ambient pressure and therefore any leakage would be in the inward direction only. This facilitates the handling and usage of highly corrosive or dangerous materials.

Since the present invention is operating at a lower pressure than prior art devices. This allows the use of construction materials which will be highly resistant to corrosive chemicals, which may not have material properties suitable for high pressure construction. The use of resilient sealing material such as "V" rings allows the use of plastic containers made with tapered molds.

The present system enables efficient reverse elution by maintaining the particle bed in a fully packed condition at all times even with motion of the bed due to changes in volume of the particulate media.

Other objects, advantages and novel features of the present invention will become apparent from the following detailed description of the invention when considered in conjunction with the accompanying drawings.

BRIEF DESCRIPTION OF THE DRAWINGS

The same elements or parts throughout the figures are designated by the same reference characters.

DETAILED DESCRIPTION OF THE PREFERRED EMBODIMENTS

Figure 1:
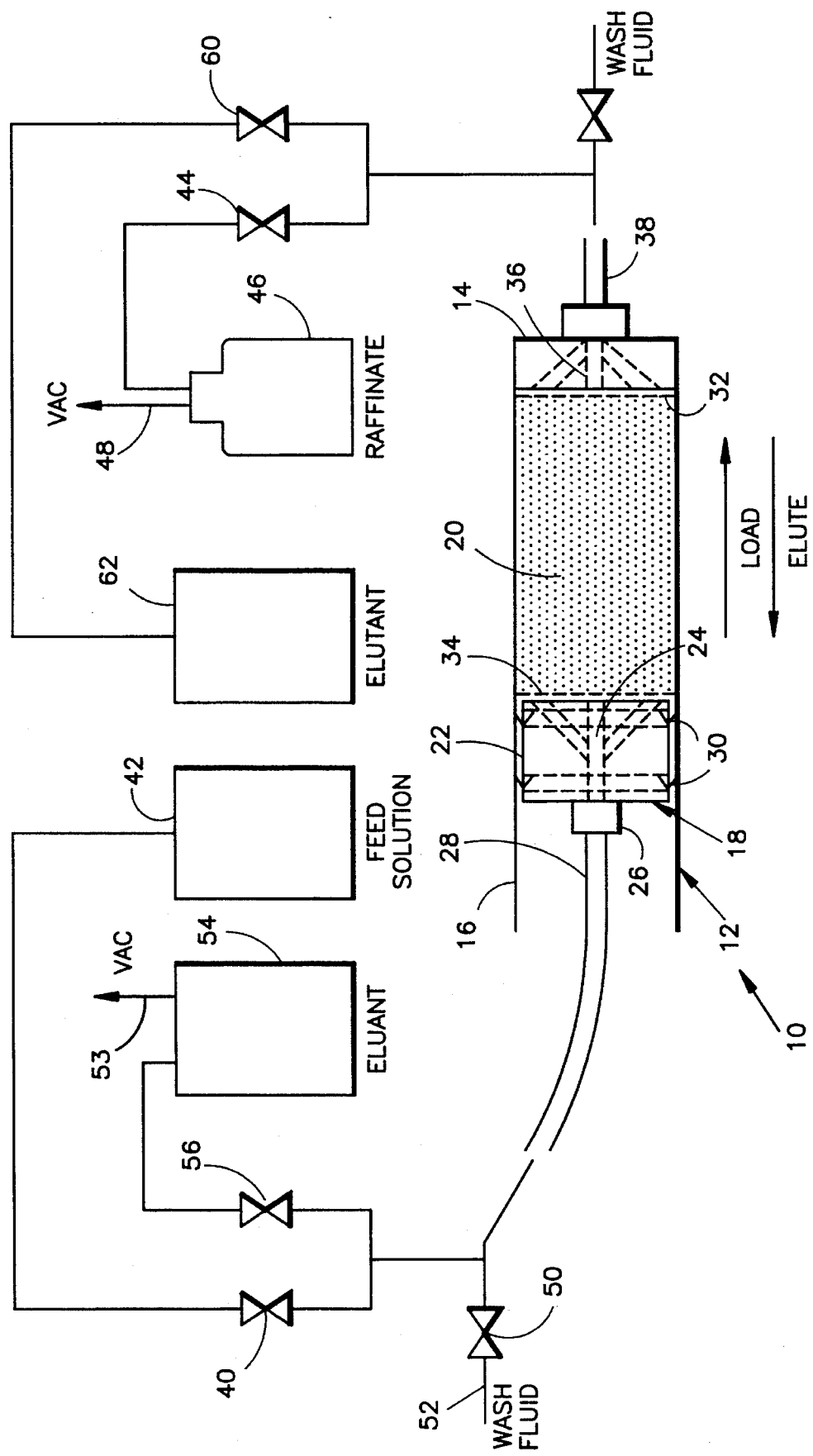
FIG. 1 is a schematic illustration, partially in cross-section, of the preferred embodiment of the present invention.

Referring to the drawings and the characters of reference marked thereon, FIG. 1 illustrates a preferred embodiment of the present invention, designated generally as 10. System 10 includes a tubular column 12 which is closed and ported at a first end 14 and open at a second end 16. A piston assembly, designated generally as 18, is supported in the column 12 for containing a bed 20 of particulate media. The particulate media 20 may comprise, for example, DOWEX-MARATHON-C™, or, a desiccant. The piston assembly 18 includes a piston 22 having a least one opening 24 for conveying a fluid through the piston 22. Means 26 are provided for attaching a fluid connection, such as flexible tubing 28 so that tubing 28 is in fluid communication with opening 24. Flexible tubing 28 is provided so that the connection 28 may move relative to the tubular column 12. A resilient seal 30 is arranged about the piston 22 to provide sealing and engagement of piston 22 and the tubular column 12 in addition to providing proper alignment therebetween. The seal may comprise, for example, a "V" ring or "O" ring. The tubular column may be substantially cylindrical or may have a longitudinal taper, being smaller at the closed end.

Porous barrier elements 32, 34 are positioned in the column 12 so as to prevent the undesired escape of particulate media through the tubular column port 36 and through the piston opening 24. Such barrier elements 34, 34 may comprise TEFLON™ brand screening material or fibrous packed material.

During loading operation, a vacuum is supplied via connection 48 to a raffinate container 46, through valve 44 to connection 38 which is in fluid communication with tubular column port 36, thereby lowering the pressure in the bed 20 below ambient, creating a differential pressure which causes the piston assembly 18 to compact the bed 20. Fluid connection 28 is connected through throttle valve 40 to a feed solution source 42. Feed solution source 42 may be, for example, digested metals in fluoroacid solutions. Feed solution from source 42 will flow through valve 40, through conduit 28, through opening 24, through barrier element 34, through bed 20, through barrier element 32, through conduit 36, out conduit 38, through valve 44, and into raffinate container 46. This flow is maintained until the resin is substantially loaded with one or more species from the feed solution. At this point, valve 40 is closed and valve 50 is opened. Flow continues with wash fluid from source 52 going through valve 50 and displacing feed solution remaining in the bed to the raffinate container 46. At this point, valve 44 and valve 50 are closed. The loading operation is complete.

Figure 2:
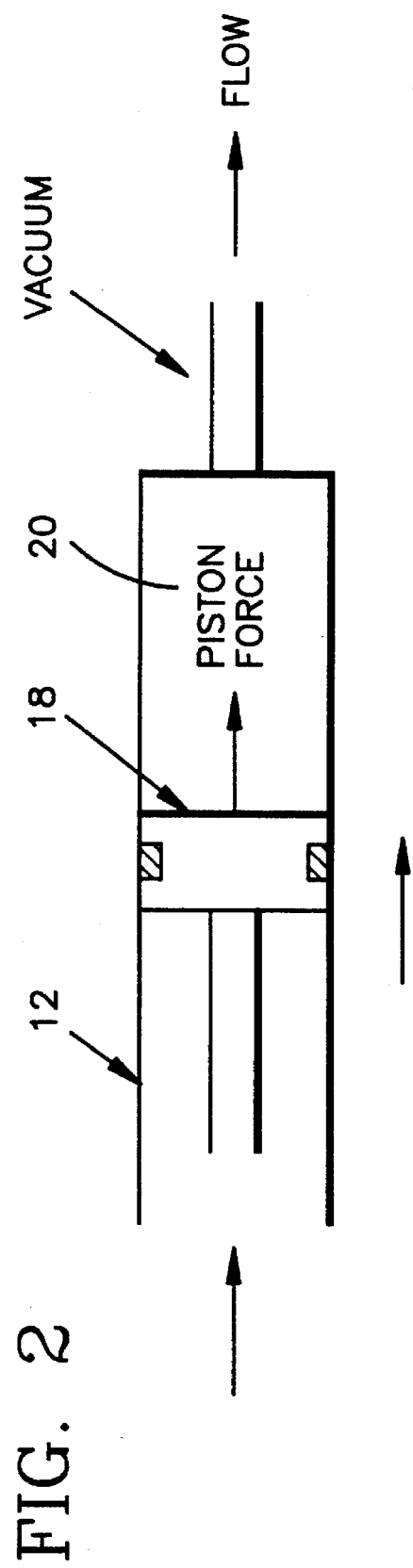
FIG. 2 is a schematic illustration of the behavior of the piston, tubular column and particulate media during loading operation.
Figure 3:
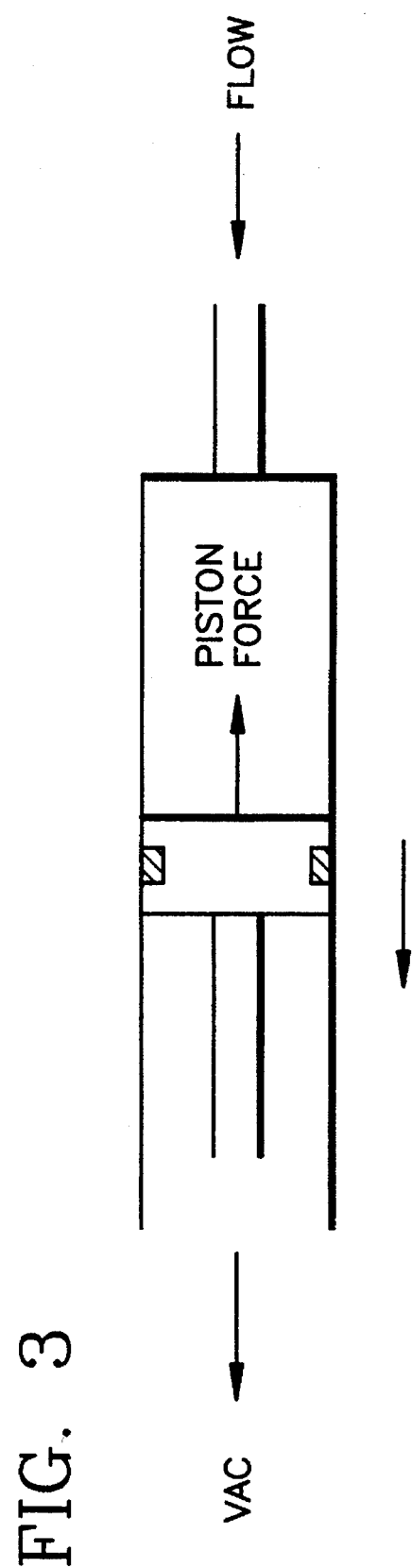
FIG. 3 is a schematic illustration of the piston, tubular column, and particulate media under the operation of reverse elution.

Referring now to FIG. 2, the behavior of the piston 18 is shown during loading operations. During this operation, the low pressure in the bed 20 causes the piston 18 to compress and pack the bed 20. The differential pressure between ambient and the bed 20 provides the force for compaction.

Having separated specific species from the feed solution 42 via the loading and washing process steps, the material retained within the bed 20 is removed by supplying a vacuum 53 to the eluant container 54. The valve 56 is opened, supplying the vacuum through flexible tubing 28, fitting 26, piston 18, to the bed 20. Valve 60 is open and throttled to provide a path for the elutant liquid from container 62 through, valve 60, conduit 38, conduit 36 to the bed 20. Flow is maintained until the absorbed species are driven off the bed 20 into the eluant tank 54. Once the species are driven off the bed 20, valve 60 is closed and wash valve 64 is opened to purge the bed of the elutants and leave it in a washed state in preparation for the next loading cycle.

In summary, four operations are involved in this preferred embodiment, in each case the apparatus being operated with vacuum so that the bed is always at a pressure less than ambient which provides for a differential pressure across the piston which supplies the force necessary to compress and pack the bed. During the loading operation, feed solution is passed through the apparatus. The bed preferentially retains one or more of the species in the feed solution. Solution flowing through the apparatus continues to the raffinate container. Loading is continued until the capacity of the bed is nearly exhausted, at which point a wash fluid is substituted for the feed solution to purge remaining feed solution from the bed to the raffinate container. The species retained by the bed are removed by flowing elutant through the apparatus and the bed opposite the direction of loading to the eluant container by means of vacuum. Unloading of the bed continues until the species retained have been exhausted from the bed, at which point the wash fluid is substituted for the elutant to remove any remaining elutant from the bed 20. At this point, the apparatus is ready for the next cycle.

Loading and eluting in this fashion leads to two advantages. The first advantage is that the bed 20 is stabilized to prevent channeling due to reverse flow. Secondly, when the species retained in the bed are eluted opposite the direction of loading, higher concentrations are obtained in the eluant fluid. Thus, less acid is required to remove the species retained by the bed.

Obviously, many modifications and variations of the present invention are possible in light of the above teachings. It is therefore to be understood that, within the scope of the appended claims, the invention may be practice otherwise than as specifically described.

What is claimed and desired to be secured by Letters Patent of the United States is:

1. A system for mechanically stabilizing a bed of particulate media which undergoes changes in volume during operation, comprising:

a) a tubular column being closed and ported at a first end and having an open second end, said tubular column containing a bed of particulate media;

b) a piston assembly supported in said column for retaining said bed of particulate media, said piston assembly, comprising:

i) a piston having at least one opening therethrough for conveying a fluid through said piston to said bed;

ii) means for attaching a fluid connection to said piston in fluid communication with said opening, wherein said fluid connection is movable relative to said tubular column;

iii) resilient sealing means arranged about said piston to provide sealing engagement of said piston and said column and to provide proper alignment therebetween; and, iv) porous barrier elements positioned in said column and defining means for preventing the undesired escape of particulate media through said tubular column port and through said piston opening;

said tubular column port and fluid connection being connectable to either a source of fluid or vacuum wherein said connection of said tubular column port and said fluid connection to either said source of fluid or vacuum defines means for drawing fluid, through said bed in either direction generally parallel to the longitudinal axis of said tubular column at a pressure below ambient, and for causing said piston to respond at said pressure below ambient to changes in volume of the particulate media so as to continually compress and compact the particulate media regardless of the direction of fluid flow.

2. The system of claim 1 wherein said fluid connection comprises flexible tubing.

3. The system of claim 1 wherein said particulate media comprises ion exchange resin.

4. The system of claim 1 wherein said resilient sealing means comprises a "V" ring.

* * * * *